United States Patent [19]

Hayward et al.

[11] Patent Number: 5,026,725
[45] Date of Patent: Jun. 25, 1991

[54] INHIBITION OF BONE LOSS BY 4-SUBSTITUTED-5-HYDROXY-2(5H)-FURANONES

[75] Inventors: Marshall A. Hayward, Lawrenceville; Joseph P. Sabatucci, Plainsboro; Ivo L. Jirkovsky, Plainsboro; Yvon Lefebvre, Plainsboro, all of N.J.

[73] Assignee: American Home Products Corporation, New York, N.Y.

[21] Appl. No.: 463,091

[22] Filed: Feb. 23, 1990

Related U.S. Application Data

[62] Division of Ser. No. 205,147, Jun. 6, 1988, Pat. No. 4,916,241.

[51] Int. Cl.$^5$ .................. A61K 31/36; A61K 31/365
[52] U.S. Cl. .................. 514/465; 514/473; 549/313
[58] Field of Search .................. 514/473, 465

[56] References Cited

U.S. PATENT DOCUMENTS 3,436,390  4/1969  Lefebvre .................. 260/239
4,839,385  6/1989  Maullem et al. .................. 514/473

FOREIGN PATENT DOCUMENTS 0209274  1/1987  European Pat. Off. .

Primary Examiner—C. Warren Ivy
Assistant Examiner—Ba K. Trinh
Attorney, Agent, or Firm—Walter Patton

[57] ABSTRACT

This invention relates to 4-substituted-5-hydroxy-2(5H)-furanones, to the process for their preparation, to pharmaceutical compositions containing said 4-substituted-5-hydroxy-2(5H)-furanones and to the use of said 4-substituted-5-hydroxy-2(5H)-furanones for modifying the balance between bone production and bone resorption in a host animal, including man.

2 Claims, No Drawings

INHIBITION OF BONE LOSS BY 4-SUBSTITUTED-5-HYDROXY-2(5H)-FURANONES This is a divisional application of copending application U.S. Ser. No. 07/205,147, filed June 6, 1988, now issued as U.S. Pat. No. 4,916,241, Apr. 10, 1990.

This invention relates to 4-substituted-5-hydroxy-2(5H)-furanones to the process for their preparation, to pharmaceutical compositions containing said 4-substituted-5-hydroxy-2(5H)-furanones and to the use of said 4-substituted-5-hydroxy-2(5H)-furanones for modifying the balance between bone production and bone resorption in a host animal, including man.

BACKGROUND OF THE INVENTION

Osteoporosis is a skeletal disorder which is evidenced by a decrease in bone density throughout the body. In fact, both the bone mineral (calcium phosphate called "hydroxyapatite") and the bone matrix (major protein called "collagen") are slowly lost. This condition may begin to occur in humans as early as age 30. In general, the process is more rapid in postmenopausal women than in men. However, after age 80 there is no sex difference in the incidence of osteoporosis. In the course of 10 to 20 years of bone loss there may be symptoms of back pain and X-ray evidence of deformation of the spine. At older ages, the brittleness of the bones becomes evident by the ease with which the proximal femur ("hip") fractures. Osteoporosis is the most common cause of fractures in people over age 45.

Although the cause of osteoporosis is poorly understood, it is believed that there is an imbalance between bone production and bone resorption (bone breakdown). Bone remains a dynamic tissue throughout the life of an animal. That is, new bone is continuously being formed and old bone is continuously being resorbed. However, in animals suffering from an osteoporotic condition, net bone resorption exceeds bone formation.

A survey indicates that in the United States there may be fifteen to twenty million people afflicted with osteoporosis [W. A. Peck (Chairman), NIH Osteoporosis Consensus Conference, J. Am. Med. Assoc., 10, 252:799–802 (1984)]. Various types of osteoporosis are designated according to special conditions believed to be causative: senile (aging); post-menopausal (female loss of estrogenesis); disuse (chronic immobilization); steroid (long term steroid treatment as in arthritis). Osteoporosis may also be manifested in dental problems since the mandible appears to lose mass more rapidly than any other bone. Thus, periodontal disease involving a loosening of the adult teeth may be an early sign of osteoporosis.

The mechanism of bone loss is at present poorly understood. Moreover, the present methods of treatment are generally unsatisfactory. These include anabolic agents, various drugs containing phosphorous, Vitamin D, calcium salts, fluorides and calcitonin.

Estrogen replacement therapy has been the therapy of choice for osteoporosis in post-menopausal women.

Physical therapy is another method currently used to treat osteoporosis since immobilization can cause osteoporosis at any age. Thus, many physicians believe that exercise and physical therapy can prevent the progression of the disease in elderly patients. However, physical therapy can be harmful for patients with fractures and, moreover, overstrenuous exercise can cause fractures in patients with severe osteoporosis.

Other treatments include the administration of a fluoride salt such as sodium fluoride which has been shown to promote bone growth clinically, apparently by stimulating collagen synthesis. However, a serious side effect is poorly calcified, irregular bone growth. Another treatment involves infusion of calcium and Vitamin D to counteract the deficiency of calcium or impaired absorption of calcium which is symptomatic in some elderly patients. There is, however, no evidence that a higher intake of calcium will prevent osteoporosis or increase bone mass in adults.

The most promising therapeutic approach to the treatment of osteoporosis is the administration of agents which have been designed to modify the balance between the rate of bone production and the rate of bone resorption in such a manner that the ratio of the former to the latter is increased, resulting in no net bone loss. After the previously occurred bone losses have been restored, a steady state is reached where the rate of bone production and rate of bone resorption are equal. Such a modification may be effected by stimulating the physiological mechanism of bone deposition, i.e., bone formation, or by retarding the mechanism of bone resorption, or both. Drugs presently in use or in the experimental stages for accomplishing these purposes include phosphonates, calcitonin and mithramycin. However, all of these drugs suffer serious drawbacks.

Mithramycin, an antibiotic, has anti-tumor activity together with hypocalcemic activity, causing a reduction of serum calcium which in turn is believed to be indicative of a decrease in the relative rate of bone resorption—i.e., bone resorption relative to bone production. Side effects, however, include renal and hepatic toxicity as well as nausea. Likewise, the organic phosphonates have side effects which include extraskeletal calcification, hypotension and renal failure. Calcitonin presents an immunological problem because it is commonly derived from a non-human source. Thus, none of the foregoing agents are at present suitable for use alone in the treatment of osteoporosis.

PRIOR ART

The closest prior art is U.S. Pat. No. 3,436,390 claiming related compounds which have steroid moieties directly attached to the hydroxyfuranone ring. Also, EP 209274 claims compounds which have retinoid type groups in the 4-position. The new invention differs from the previously disclosed art in two major points:

1. The presence of the hydroxyl ethyl group or the methylene group in position 4, separating the hydroxyfuranone and a substituted benzene ring.

2. Biological activity - the previously patented compounds are all claimed as anti-inflammatory agents.

SUMMARY OF THE INVENTION

This invention relates to novel 4-substituted-5-hydroxy-2(5H)-furanone derivatives useful in inhibiting bone resorption and having the formula (I)

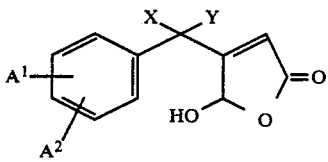

$$\text{(I)}$$

wherein X is hydrogen or hydroxy; Y is hydrogen or lower alkyl containing 1 to 6 carbon atoms; $A^1$ and $A^2$ are independently selected from the group consisting of phenyl, OR, OAr, or halogen wherein R is lower alkyl containing 1 to 6 carbon atoms or $A^1A^2$ represents —$OCH_2O$—.

Preferred compounds of the present invention are those of formula (I) wherein X is hydroxy; Y is —$CH_3$ and $A^1$ and $A^2$ are as defined above or X and Y are both hydrogen and $A^1$ and $A^2$ are as defined above.

The most preferred compounds of the present invention are designated

4-[1-([1,1′-biphenyl]-4-yl)-1-hydroxyethyl]-5-hydroxy-2(5H)-furanone produced by Scheme 1;
5-hydroxy-4-[1-hydroxy-1-[3,4-methylenedioxyphenyl-]ethyl]-2(5H)-furanone produced by Scheme 1;
4-[1-([1,1′-biphenyl]-4-yl)methyl)-5-hydroxy-2(5H)-furanone produced by Scheme 2;
5-hydroxy-4-([3,4-methylenedioxyphenyl]methyl)-2(5H)-furanone produced by Scheme 2;
5-hydroxy-4-[1-hydroxy-1-(4-phenoxyphenyl)ethyl]-2(5H)-furanone produced by Scheme 1;
5-hydroxy-4-[1-hydroxy-1-[3,4-dimethoxyphenyl]ethyl]-2(5H)-furanone produced by Scheme 1;
5-hydroxy-4-[1-hydroxy-1-[4-methoxy-3-bromophenyl-]ethyl]-2(5H)-furanone produced by Scheme 1; and
5-hydroxy-4-[1-hydroxy-1-[4-chlorophenyl]ethyl]-2(5H)-furanone produced by Scheme 1.

The compounds of this invention possess an assymetric carbon atom and thus are made as racemic mixtures. The d and l enantiomorphs in these racemic mixtures are included within the scope of the present invention.

It is another object of this invention to provide an improved process for the production of 4-substituted-5-hydroxy-2(5H)-furanones according to Scheme 1 and 2.

SCHEME 1

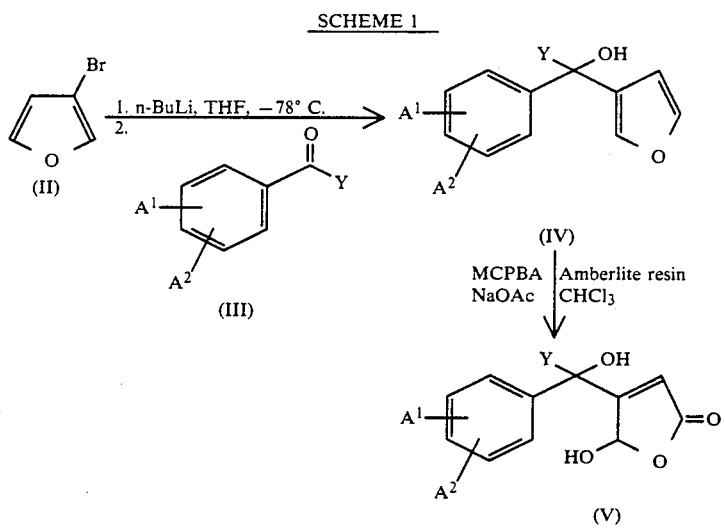

wherein Y is hydrogen or lower alkyl containing 1 to 6 carbon atoms and $A^1$ and $A^2$ are as defined above.

SCHEME 2

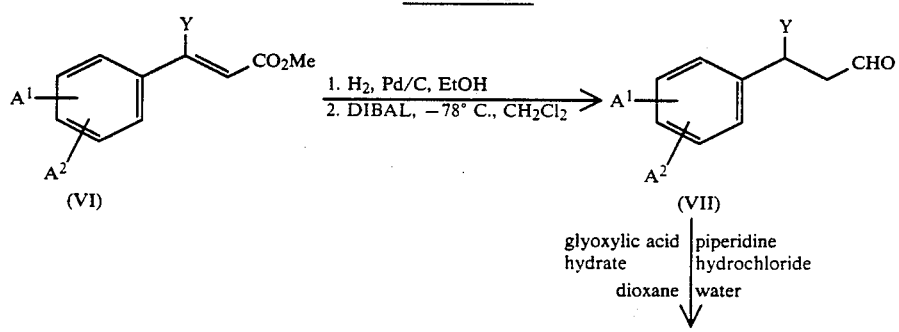

SCHEME 2

-continued

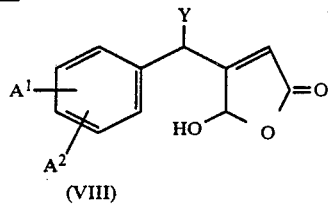

(VIII)

The synthesis of the title products is depicted in Schemes 1 and 2. Furans of type (IV) may be made by reacting the anion of 3-bromo furan with an appropriately substituted phenone derivative of type (III). The furan is then converted into the desired product (V) by oxidation with m-chloroperbenzoic acid (MCPBA) in the presence of an acidic substance such as acetic acid or Amberlite IR-120 acidic resin.

Cinnamates of type (VI) are transformed into the corresponding aldehydes of type (VII) by methods known in the art such as those described by Fleming and Woolias, J. Chem. Soc. Perkin I, (3) 829 (1979). Especially useful for this transformation is the reduction of the aforementioned cinnamates by hydrogenation over a palladium on carbon catalyst followed by a further reduction of the ester moiety by diisobutyl aluminum hydride (DIBAL). The aldehyde (VII) can then be converted into the desired furanone (VIII) following the procedure described by Wermuth and Bourguignon, J. Org. Chem., 46, 4889 (1981).

It is another object of this invention to provide a method whereby a host animal, including man, suffering from osteoporosis is treated in order to modify the balance between the rates of bone deposition and bone resorption in said host animal whereby the ratio of the latter to the former is reduced.

It is another object of this invention to provide a process for the treatment of a host animal in order to prevent the deterioration of existing healthy bone tissues in said host animal. It is possible that these agents could also be of utility in the treatment of hypercalcemia of malignancy, Paget's disease, and the arthritides.

It is a further object of this invention to provide a process for the treatment of periodontal disease.

DETAILED DESCRIPTION OF THE INVENTION

Bone is degraded during the process of bone resorption and this leads to the subsequent development of osteoporosis. The present invention provides a method for the treatment of a host animal in order to modify the balance between the rate of bone resorption and the rate of bone deposition in said host animal whereby the ratio of said rate of bone resorption to said rate of bone deposition is reduced, comprising administering to said host animal an amount, sufficient to modify said balance and reduce said ratio, of 4-substituted-5-hydroxy-2(5H)-furanones. 4-Substituted-5-hydroxy-2(5H)-furanones would be administered to humans at a daily dose of 200 mg to 1200 mg.

The ability of 4-substituted-5-hydroxy-2(5H)-furanones to modify the process of bone resorption was evaluated essentially as described by G. Eilon, L. G. Raisz: "Comparison of the effects of stimulators and inhibitors of resorption on the release of lysosomal enzymes and radioactive calcium from fetal bone in organ culture," Endocrinology 103:1969–1975 (1978). 4-Substituted-5-hydroxy-2(5H)-furanones evidence activity as inhibitors of $^{45}$Ca-bone resorption in vitro at concentrations of 0.1 to 10.0 μg/mL.

The advantageous effects of 4-substituted-5-hydroxy-2(5H)-furanones and specifically 4-[1-([1,1'-biphenyl]-4-yl)-4-hydroxyethyl]-5-hydroxy-2(5H)-furanone in preventing bone loss in accordance with the present invention are demonstrated by the following experimental results.

4-[1-([1,1'-Biphenyl]-4-yl)-1-hydroxyethyl]-5-hydroxy-2(5H)-furanone was examined for its effects in two distinct rodent models of bone demineralization. Significant bone sparing activity was observed with 4-[1-([1,1'-biphenyl]-4-yl)1-hydroxyethyl]-5-hydoxy-2(5H)-furanone at 25 mg/kg i.p. in an immobilization dependent model of osteopenia in the rat femur. In a model of cancellous bone loss performed in ovariectomized rats, significant retention of bone resulted from the treatment of rats with 4-[1-([1,1'-biphenyl]-4-yl)-1-hydroxyethyl]-5-hydoxy-2(5H)-furanone at doses of 10 mg/kg i.p. over a 6 week period.

The compounds of formula (I) of this invention are used alone or in combination with pharmacologically acceptable carriers, the proportion of which is determined by the solubility and chemical nature of the compound, chosen route of administration and standard medical practice. For example, they are administered orally in the form of capsules, tablets, suspensions or solutions or they may be injected parenterally. Capsules and tablets are the preferred mode of administration. For parenteral administration they can be used in the form of a sterile solution containing other solutes, for example enough saline or glucose to make the solution isotonic.

The capsule and tablet compositions contain the active ingredient in admixture with non-toxic pharmaceutical excipients known to be suitable in the manufacture of capsules and tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula (I) contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil for example, oil for example, arachis oil, olive oil, sesame oil, or coconut oil, or in mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula (I) will vary with the form of administration and the particular compound chosen. Furthermore, it will vary with the particular host as well as the age, weight and condition of the host under treatment, as well as with the nature and extent of the symptoms. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. For example, the effective amount of the compounds for oral administration can usually range from about 200 mg to 1200 mg/day in single or divided doses although, as aforementioned, variations will occur. However, a dosage level that is in the range of from about 500 mg to 900 mg/day in single or divided doses is employed most desirably for oral administration in order to achieve effective results.

The following examples are provided to illustrate the methods of preparation and testing of the compounds of the present invention. These examples are not meant to be considered, in any way, as limitations of the breadth and scope of the present invention. The temperatures expressed in these examples are in degrees centigrade.

EXAMPLE 1

Scheme 1

4-[1-([1,1'-Biphenyl]-4-yl)-1-hydroxyethyl]-5-hydroxy-2(5H)-furanone

Step (1) Preparation of α-([1,1'-Biphenyl]-3-yl)-α-methyl-3-furanmethanol

To a solution of 14.5 g (0.1 mol) of 3-bromofuran in 500 mL of THF cooled to −78° C. was added dropwise a solution of 64 mL (0.12 mol) to n-butyl lithium in THF. The solution was allowed to stir for 3 hours after the addition was complete, whereupon a solution of 19 g (0.1 mol) 4-acetylbiphenyl in 200 mL of THF was added. The mixture was allowed to stir for 1 hour, then warmed to room temperature. The mixture was then poured into water and extracted with ether (2×500 mL). The ether layers were combined, dried (MgSO$_4$) and concentrated to afford 19.5 g of crude solid. The solid was recrystallized from ether:hexane to afford 12.5 g, 47% of light yellow solid, m.p. 108°-109° C.

NMR (CDCl$_3$, 200MHz): δ 7.61-7.88 (m, 11H, ArH), 6.34 (t, J=2Hz, 1H, HC=CO), 1.92 (s, 3H, CH$_3$).

Step (2) Preparation of 4-[1-([1,1'-Biphenyl]-4-yl)-1-hydroxyethyl]-5-hydroxy-2(5H)-furanone α-([1,1'-Biphenyl]-3-yl)-α-methyl-3-furanmethanol (10.8 g, 0.041 mol) was dissolved in 200 mL of chloroform, then 9.9 g (0.12 mol) of NaOAc and 1 g of Amberlite IR-120 acidic resin was added. The mixture was cooled to 0° C., whereupon 18 g (0.087 mol) of m-chloroperbenzoic acid (MCPBA) was added portionwise over the course of 15 minutes. After stirring the solution for 3 hours the solids were removed by filtration through Celite, and the filtrate washed once with 200 mL of 5% aqueous NaHCO$_3$. The aqueous layer was separated and extracted with chloroform (2×100 mL). The solution was dried (MgSO$_4$) and concentrated and the residue chromatographed over SiO$_2$ (300 g). Elution first with 40% EtOAc-hexane then with 60% EtOAc-hexane yielded 3.9 g of solid, which was recrystallized from EtOAc-hexane to afford 3.2 g (26%) analytically pure product, as an inseparable mixture of diastereomers (7:3 ratio) m.p. 179°-182° C.

NMR (400MHz, DMSO) Diastereomer 1: δ 7.79 (d, 1H, OH), 7.63 (m, 3H, ArH), 7.54 (m, 2H, ArH), 7.45 (m, 2H, ArH), 7.34 (m, 2H, ArH), 6.26 (s, 1H, HC=C), 5.86 (d, J=7Hz, 1H, OCH), 1.76 (s, 3H, CH$_3$).

Diastereomer 2: δ 7.67 (d, J=8Hz, 1H, OH), 7.63 (m, 3H, ArH), 7.54 (m, 2H, ArH), 7.45 (m, 2H, ArH), 7.34 (m, 2H, ArH), 6.19 (d, J=8Hz, 1H, OCH), 5.92 (s, 1H, HC=C), 1.76 (s, 3H, CH$_3$).

IR: 3480 (OH), 1755 (C=O) cm$^{-1}$.

Anal. Calcd. for C$_{18}$H$_{16}$O$_4$: C, 72.95; H, 5.44, Found: C, 72.92; H, 5.16.

EXAMPLE 2

Scheme 2

Preparation of 5-Hydroxy-4-([3,4-methylenedioxyphenyl]methyl)-2(5H)-furanone 2.5 g (0.027 mol) of glyoxylic acid hydrate, 3.2 g (0.027 mol) of piperidine hydrochloride, and 30 mL of dioxane were mixed with stirring, whereupon water was added in dropwise fashion until a homogeneous solution resulted. 3-(3,4-Methylenedioxyphenyl)propionaldehyde (4.8 g, 0.027 mol) was then introduced and the solution allowed to stir at room temperature for 1 hour, then heated at reflux for 48 hours. At the end of this time the solution was concentrated, diluted with water, and extracted with EtOAc (2×100 mL). The organic layer was separated, dried (MgSO$_4$) then concentrated to afford an oil. The crude oil was chromatographed over silica gel (150 g). Elution with 50% EtOAc-hexane afforded 1.8 g, 28% of the desired product as a light yellow oil.

NMR (400MZ, CDCl$_3$): δ 6.76 (d, J=8Hz, 1H, H5), 6.65 (s, 1H, H2), 6.63 (d, J=8Hz, 1H, H6), 5.97 (s, 1H, C=CH), 5.96 (s, 2H, OCH$_2$O), 5.70 (s, 1H, OCH), 3.75 (d, J=17Hz, 1H, ArCH), 3.52 (d, J=17Hz, 1H, ArCH).

IR: 3600 (OH), 1770 (C=O)cm$^{-1}$.

MS: m/e 234 (52, M+), 188 (20, M—CH$_2$O$_2$), (100, M—C$_5$H$_5$O$_3$).

EXAMPLE 3

Immobilization Dependent Bone Loss in the Rat Femur

This assay was performed according to a modification of a procedure described by A. D. Kenny, "Role of Carbonic Anhydrase in Bone: Partial Inhibition of Disuse Atrophy of Bone by Parenteral Acetazolamide," Calcif. Tissue Int., 37 ,126–133(1985).

Bone mass was determined in contralateral femora from ovariectomized rats which had been subjected to unilateral sciatic nerve severence. After sciatic neurotomy, the rats were treated with 4-[1([1,1'-biphenyl]-4-yl)-1-hydroxy-ethyl]-5-hydroxy-2(5H)-furanone for a total of 4 weeks. Rats were euthanized, then femora were excised, debrided of soft tissue, then dehydrated. After drying, the mass of each pair of femora was determined by weighing. The bone mass data is summarized in Table 1, which demonstrates the significant retention of bone in immobilized femora in rats treated with 4-[1-([1,1'-biphenyl]-4-yl)-1-hydroxyethyl]-5-hydroxy-2-(5H)-furanone relative to femora from vehicle treated control rats.

TABLE 1

Effect of 4-[1-([1,1'-Biphenyl]-4-yl)-1-hydroxyethyl]-5-hydroxy-2-(5H)-furanone on Bone Loss in Immobilization Dependent Osteoporosis

| Treatment | Regimen 5×/week for 4 weeks | (n) | Control Femur | Immobilized Femur | Difference | % Change in Femur mass |
|---|---|---|---|---|---|---|
| Study 1 | | | | | | |
| Vehicle | 0.2–0.3 mL/rat i.p. | 9 | 439.4 ± 14.0 | 393.3 ± 11.8 | 46.1 ± 6.2 | 10.49 |
| 4-[1-([1,1'-biphenyl]-4-yl)-1-hydroxyethyl]-5-hydroxy-2(5H)-furanone | 50 mg/kg, i.p. | 9 | 417.8 ± 7.8 | 390.6 ± 8.6 | 27.2 ± 3.4* | 6.51* |
| Study 2 | | | | | | |
| Vehicle | 0.3 mL/rat, i.p. | 8 | 497.4 ± 10.7 | 433.1 ± 11.4 | 54.3 ± 5.9 | 10.92 |
| 4-[1-([1,1'-biphenyl]-4-yl)-1-hydroxyethyl]-5-hydroxy-2(5H)-furanone | 5 mg/kg, i.p. | 6 | 475.8 ± 10.2 | 433.7 ± 7.4 | 42.2 ± 7.4 | 8.76 |
| 4-[1-([1,1'-biphenyl]-4-yl)-1-hydroxyethyl]-5-hydroxy-2(5H)-furanone | 10 mg/kg, i.p. | 8 | 488.6 ± 17.8 | 443.4 ± 5.0 | 45.3 ± 14.4 | 8.70 |
| 4-[1-([1,1'-biphenyl]-4-yl)-1-hydroxyethyl]-5-hydroxy-2(5H)-furanone | 25 mg/kg, i.p. | 8 | 478.1 ± 7.6 | 449.5 ± 11.3 | 28.6 ± 5.3* | 6.07* |
| 4-[1-([1,1'-biphenyl]-4-yl)-1-hydroxyethyl]-5-hydroxy-2(5H)-furanone | 50 mg/kg, i.p. | 7 | 443.6 ± 37.2 | 421.1 ± 11.9 | 22.4 ± 4.1* | 4.97* |

*$p < 0.05$ vs corresponding vehicle control valve

EXAMPLE 4

Ovariectomy Dependent Cancellous Bone Loss in the Tibia

This assay was performed in an experimental model based on the work described by T. J. Wronski, P. L. Lowry, C. C. Walsh and L. A. Ignaszewski, "Skeletal Alteration in Ovariectomized Rats," Calcif. Tissue Int., 37, 324–328 (1985).

Cancellous bone content was determined in the proximal metaphysis of rats which had been subjected to ovariectomy for a period of 8 weeks. Two weeks after ovariectomy, treatment with 4-[1-(1,1'-biphenyl]-4-yl)-1-hydroxyethyl]-5-hydroxy-2-(5H)-furanone i.p. (or an equivalent injection of vehicle) was initiated and continued for 6 weeks. Animals received treatment 5 days on/2 days off per week. Rats were euthanized, then tibia were excised, fixed, and processed for histological assessment. The bone mineral present within the proximal metaphysis was quantified with a computer-assisted image analysis system. The region of bone mineral quantitation in the proximal tibia selected for cancellous bone content evaluation are the primary and secondary spongiosa. To select and standardize this area for evaluation, the epiphyseal growth plate-metaphyseal junction is oriented parallel to the abscissa of the digitizing screen. Bone elements 1.7 mm (secondary spongiosa) and 0.2 mm (primary spongiosa) from the growth plate and equidistant from the flanking cortical elements are then quantified as described above. The total area evaluated is 2.3 mm wide and 1.45 mm deep, constituting a 3.34 mm² area. Treatment of rats with 4-[1-(1,1'-biphenyl]-4-yl)-1-hydroxyethyl]-5-hydroxy-2-(5H-furanone at 10 and 25 mg/kg demonstrated significant bone mineral retention relative to vehicle treated control animals. Summary data is compiled in Table 2.

TABLE 2

Effect of 4-[1-([1,1'-Biphenyl]-4-yl)-1-hydroxyethyl]-5-hydroxy-2(5H)-furanone on Bone Loss as Judged by Histological Assessment of Cancellous Bone Within the Proximal Tibia in Ovariectomy Dependent Osteopenia in Rats

| Treatment | (n) | Primary Spongiosa | Secondary Spongiosa |
|---|---|---|---|
| Vehicle | (7) | 16.4 ± 2.2 | 7.4 ± 1.4 |
| 4-[1-([1,1'-biphenyl]-4-yl)-1-hydroxyethyl]-5-hydroxy-2(5H)-furanone 2 mg/kg i.p. | (6) | 18.8 ± 2.5 | 9.6 ± 1.7 |
| 4-[1-([1,1'-biphenyl]-4-yl)-1-hydroxyethyl]-5-hydroxy-2(5H)-furanone 10 mg/kg i.p. | (7) | 22.9 ± 1.3* | 12.8 ± 1.5* |
| 4-[1-([1,1'-biphenyl]-4-yl)-1-hydroxyethyl]-5-hydroxy-2(5H)-furanone 25 mg/kg i.p. | (7) | 23.1 ± 2.1* | 13.5 ± 1.8* |

*$p < 0.01$ vs Vehicle Group

The administration of 4-[1-([1,1'-biphenyl]-4-yl)-1-hydroxyethyl]-5-hydroxy-2-(5H)-furanone in accordance with this invention can be supplemental to other regimens for the treatment of osteoporosis or periodontitis. For example, the administration of 4-[1-([1,1'-biphenyl]-4-yl)-1-hydroxyethyl]-5-hydroxy-2-(5H)-furanone can be supplemental to the 600 mg to 1200 mg daily intake of calcium as calcium phosphate or calcium carbonate. Also, the administration of 4-[1-([1,1'-biphenyl]-4-yl)-1-hydroxyethyl]-5-hydroxy-2-(5H)-furanone can be supplemental to estrogen replacement therapy such as 0.625 mg daily of conjugated equine estrogen.

We claim:

1. A method for the treatment of a host animal in order to modify the balance between the rate of bone resorption and the rate of bone formation in said host animal whereby the ratio of said rate of bone resorption to said rate of bone formation is reduced, comprising administering to said host animal an amount of a compound of formula

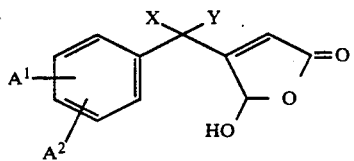

wherein X is hydroxy; Y is lower alkyl containing 1 to 6 carbon atoms; $A^1$ and $A^2$ are independently selected from the group consisting of phenyl, OR, OAr, or halogen wherein R is lower alkyl containing 1 to 6 carbon atoms or $A^1A^2$ represents —$OCH_2O$— sufficient to modify said balance and reduce said ratio.

2. The method of claim 1 wherein the said compound of formula (I) is administered at a daily dose ranging from 200 mg to 1200 mg.

* * * * *